United States Patent [19]

Crouch et al.

[11] Patent Number: 6,004,767
[45] Date of Patent: Dec. 21, 1999

[54] ASSAY AND KIT FOR DETERMINING THE CONDITION OF CELLS

[75] Inventors: Sharon Patricia Mary Crouch; Kevin John Slater, both of The Park; David Peter Sowter, Hucknall, all of United Kingdom

[73] Assignee: BTG International Limited, London, United Kingdom

[21] Appl. No.: 09/326,578

[22] Filed: Jun. 7, 1999

Related U.S. Application Data

[63] Continuation of application No. PCT/GB97/03556, Dec. 24, 1997.

[30] Foreign Application Priority Data

Dec. 24, 1996 [GB] United Kingdom ............... 9626932

[51] Int. Cl.$^6$ .............. C12Q 1/66; C12Q 1/00; C12Q 1/37
[52] U.S. Cl. ............ 435/8; 435/8; 435/4; 435/23; 435/975
[58] Field of Search ............... 435/8, 4, 23, 975, 435/29

[56] References Cited

U.S. PATENT DOCUMENTS

| | | | |
|---|---|---|---|
| 4,303,752 | 12/1981 | Kolehmainen et al. | 435/8 |
| 4,665,022 | 5/1987 | Schaeffer et al. | 435/8 |
| 4,861,709 | 8/1989 | Ulitzur et al. | 435/8 |
| 5,004,684 | 4/1991 | Simpson et al. | 435/8 |
| 5,093,238 | 3/1992 | Yamashoji et al. | 435/4 |
| 5,366,867 | 11/1994 | Kawakami et al. | 435/8 |
| 5,627,042 | 5/1997 | Hirose et al. | 435/8 |
| 5,648,232 | 7/1997 | Squirrell | 435/8 |

FOREIGN PATENT DOCUMENTS

| | | |
|---|---|---|
| 0133681 | 7/1984 | European Pat. Off. |
| 0 500 099 | 2/1992 | European Pat. Off. |
| 0 794 260 | 3/1997 | European Pat. Off. |
| 1322464 | 7/1973 | United Kingdom |
| 1446298 | 3/1974 | United Kingdom |
| 2 293 449 | 4/1995 | United Kingdom |
| WO 94/16071 | 1/1994 | WIPO |
| WO 94/17198 | 1/1994 | WIPO |

OTHER PUBLICATIONS

Derwent Patents Abstract, WPI Abstract Acc. No. 91–292634/199140 abstracting JP03195513 A.

Kimmich et al., "Assay of Picomole Amounts of ATP, ADP, and AMP Using the Luciferase Enzyme System", Anal. Biochem 69, 187–206 (1975) Month Not Available.

Orlando et al., "ATP and ADP Content of Human Ejaculated Spermatozoa", Int. J. Andrology 5, 497–502 (1982) No Month Available.

Lundin et al., "Estimation of Biomass in Growing Cell Lines by Adenosine Triphosphate Assay", Methods in Enzymology 133, 27–42 (1986) No Month Available.

Crouch et al., "The Use of ATP Bioluminescence as a Measure of Cell Proliferation and Cytotoxicity", J. Immunol. Methods 160, 81–88 (1993) No Month Available.

Morshedi et al., "Investigation of Some Biochemical and Functional Effects of Cyropreservation of Human Spermatozoa Using an Automated Freezing–Quick–Thawing Method", Int. J. Andrology 18, 279–286 (1995) No Month Available.

A. Lundin, "Clinical Applications of Luminometric ATP Monitoring" Thesis, Stockholm 1990, Clinical Research Centre, Karolinska Institute, Stockholm, Huddinge University Hospital F61, S–141 86 Huddinge, Sweden No Month Available.

*Primary Examiner*—Louise N. Leary
*Attorney, Agent, or Firm*—Nixon & Vanderhye

[57] ABSTRACT

The present invention relates to a method of assay and a kit for carrying out the assay for determining the physical condition of biological cells in vitro. The assay method distinguishes whether cells are alive and proliferating or are dying and, if dying, whether the cells are in an apoptotic or necrotic condition.

20 Claims, 6 Drawing Sheets

ASSAY AND KIT FOR DETERMINING THE CONDITION OF CELLS

This is a continuation of PCT application PCT/GB97/03556, filed Dec. 24, 1997.

BACKGROUND OF THE INVENTION

1. Field of the Invention

The present invention relates to an assay, and kit for carrying out the assay, for determining the physical condition of biological cells in vitro. Particularly, it distinguishes whether cells are alive and proliferating or are dying and, if dying, whether they are in an apoptotic or necrotic condition.

2. Description of the Related Art

Many different cell types are used for the screening of chemical compounds as prospective drugs. Prospective drugs are added to cell cultures in micotitre plates at various concentrations in duplicate or triplicate, so that the average microtitre plate is used to test for many different drugs. After the cells have been incubated for a period of time (depending on the cell type, but usually several days), the effect of the prospective drug on the cells in each well is determined.

The pathway leading to cell death, is important. Cell death may follow two distinct modes: apoptosis and necrosis. Apoptosis is the normal mode and is an active intrinsically controlled process in which the cell commits suicide in response to a wide range of physiological and toxicological signals. It occurs during embryonic development as well as in the adult, controlling immune systems and tissue turnover to regulate a stable balance of tissue mass. Apoptosis also occurs in response to an altered environment, including depletion of growth factors, serum or oxygen and upon exposure to harmful stimuli such as radiation and hyperthermia. Apoptotic cells are removed in vivo by phagocytosis from neighbouring cells and macrophages without invoking an inflammatory response. Necrosis, on the other hand, is a passive pathological event that occurs under severe conditions causing sudden cellular damage and significant loss in tissue architecture. Necrotic cells release their cytoplasmic contents into the extracellular fluid, generating an inflammatory reaction. In in vitro conditions, there is no rapid removal mechanism of apoptotic cells, and so the cells accumulate and ultimately undergo necrotic cell death. Necrotic cell death in these circumstances is termed "secondary necrosis". Ordinary necrosis is termed "primary necrosis".

A determination of the effect of a treatment on the pathway leading to cell death is vital if screening for therapeutic agents is to be successful.

As mentioned above, it is now known that normal cells die by apoptosis, a predetermined pathway which is encoded genetically. Cancer cells have been shown to possess one or more defects which prevent normal cell death from occurring. These defects allow cancer cells to proliferate in an uncontrolled manner.

An assay for determining whether a treatment caused a cancer cell line to undergo cell death by apoptosis is valuable, since it allows one to determine whether or not a treatment can cause the cells to switch back to the normal apoptotic pathway mechanisms of cell death. Such a treatment would of course be preferable to whole scale cytotoxic drugs which may kill normal as well as cancer cells.

In other conditions, such as Alzheimer's Disease, the basis of the condition is cell death. A screening method which can determine whether or not a treatment causes cellular proliferation helps to identify drugs which could correct the cell death exhibited by the condition.

Very potent apoptotic agents may be overlooked because they appear to cause necrosis rather than apoptosis, when in fact they cause apoptosis quickly and the necrosis detected is secondary necrosis which follows apoptosis. It is therefore valuable to detect secondary necrosis.

One of the most significant and early events in necrosis is swelling of mitochondria (hydropic swelling), which is reversible in the early stages providing the causative agent is removed or reversed. However, beyond a certain point the cell will die, and unlike apoptosis, the cells swell, the plasma membrane becomes leaky, resulting in uncontrolled release of the cells constituents such as proteolytic enzymes and inflammatory mediators. In vivo, these substances trigger an inflammatory response in the tissue, resulting in permanent uncontrolled damage, which in certain situations may prove life-threatening.

The feature of a leaky plasma membrane is the basis of a test using propidium iodide (PI) with flow cytometry and allows the viability of the cells to be tested: necrotic cells will stain but apoptotic cells (except in the later stages of apoptosis), or proliferating cells will not. DNA fragmentation in necrosis is not as extensive as in apoptosis and is heterogeneous in size, resulting in a smear on gel electrophorsis. This difference in DNA fragmentation is the basis for the "TUNEL" (Terminal deoxytransferase deoxy Uridine triphosphate-mediated Nick End Labelling) technique which probably represents the best method for determining apoptosis at present and allows differentiation between necrosis and apoptosis. The problem with this method (apart from the very high cost of the equipment) is that it cannot be automated and a set of 20 samples takes up to three hours to prepare, measure and analyse. It is therefore totally unsuitable for screening purposes.

Primary necrosis differs from secondary necrosis in that primary necrosis results in the features detailed above, while necrosis secondary to apoptosis results in increased uptake of the TUNEL label initially, followed by increased uptake of the PI stain due to a leaky plasma membrane in the latter stages of the process.

All of the available methods are limited by the inherent problems of the flow cytometry technology and therefore are not suitable for large scale or high throughput screening.

It is a problem that there are currently no methods available for high throughput assay of the condition of cells, particularly for use in small assay volumes, as in wells of microtitre plates.

SUMMARY OF THE INVENTION

It has now surprisingly been found that the above problem can be solved by making use of the bioluminescent reaction between luciferin or a derivative thereof, a luciferase and cellular ATP.

Thore, *Science Tools,* 26, 30–34 (1979), teaches that the initial rapid light emission phase of the luciferase reaction is the most reliable measure of ATP concentration. Conventional bioluminescent assay techniques therefore require measurements to be taken as soon as possible after the addition of luciferase and luciferin, before any signal decay occurs. The present inventors have observed that the light emission does not fade entirely, but eventually reaches a substantially constant condition.

The above phenomenon is explicable by assuming that the luciferase molecule has two binding sites for ATP. The first binding site has a high affinity for ATP and is responsible for the flash reaction, but appears to be inhibited by the product of the reaction. The second binding site has a low affinity for ATP and may be responsible for the prolonged substantially constant light emission that follows the initial flash.

The present invention exploits the observed biphasic response of luciferase, taking advantage of the fall in concentration of ATP after the initial glow or flash. At this low and substantially constant ATP level, it becomes possible to measure cellular ADP, by adding to the bioluminescent reaction reagent(s) which convert ADP to ATP and taking measurements of light intensity before and after this reaction or, more generally, at any two time points which capture an increase in light intensity sufficient to give an indication of the cellular ADP level. By taking measurements during this second, substantially constant, light phase of the luciferase reaction, it is possible to overcome all the problems associated with high ATP concentrations which can occur in the small reaction volumes demanded by microtitre plate technology.

According to a first aspect, the invention provides a method of assay of the physical condition of a sample of biological cells in vitro, in a medium for maintaining the cells, comprising:

(a) adding to the sample an agent which releases adenylate nucleotides from the interior of the cells to be assayed into the medium containing the cells;

(b) simultaneously or subsequently adding to the sample a bioluminescent reagent comprising luciferin or a derivative thereof and a luciferase, said luciferin or derivative thereof emitting light in a bioluminescent reaction with the luciferase in the presence of ATP;

(c) after said addition, using the emitted light or its change with respect to time elapsed, to determine an ATP concentration;

(d) after the initial light intensity has reached a substantially constant level, adding a reagent which converts ADP to ATP;

(e) using light emitted thereafter or its change with respect to time elapsed to determine an ADP concentration; and (f) using information from the ADP and ATP concentrations thus determined to determine the condition of the cells.

Preferably step (c) involves measuring the intensity of the emitted light so as to determine an ATP concentration, said measurement being designated A. Step (e) is then carried out by an operation comprising:

(i) at the time of adding the ADP-converting reagent or immediately before or immediately thereafter, measuring the intensity of the emitted light, said measurement being designated B;

(ii) subsequently, when cellular ADP has been converted to ATP, measuring the intensity of emitted light at a level C;

(iii) from the difference C–B determining an ADP concentration;

and step (f) comprises using information from the ADP concentration as represented by measurement C–B and the ATP concentration as represented by A, to determine the condition of the cells.

The term "substantially constant" used herein in relation to emitted light intensity means that it varies only slightly over the same time period as is taken to carry out the light intensity measurements. As a non-limiting example, the term is intended to include the meaning that the rate of change of emitted light intensity is less than 5% per minute, preferably less than 3% per minute. In any event the person skilled in the art will be able to appreciate whether the level is sufficiently constant to be able to obtain a valid reading of the ATP produced by adding the ADP-converting reagent, not significantly affected by any small change in the ATP baseline.

The measurement C can be any which gives a measure of ADP which fairly reflects the amount of ADP accumulated in the cells after allowing adequate time for the conversion of ADP to ATP to take place. In apoptotic or necrotic cells, C is greater than B. Generally stated, C is a level or a "plateau" of intensity of emitted light, where the intensity varies at a rate of less than 3% per minute.

The concentrations of ADP and ATP can be used in any way to determine cell condition, for example as absolute values from which matrices can be developed, or in various mathematical relationships. However, the concentrations of ADP (preferably given by C–B) and ATP (preferably given by A) are preferably expressed as a ratio of ADP to ATP and the viability status of the cells of the sample can be determined based either on a predetermined value of this ADP to ATP ratio for the particular cell type under investigation or by numerical ranges which apply to most types of cell likely to be encountered in the samples.

The invention also includes a kit for carrying out an assay of the physical condition of a sample of biological cells in vitro, in a medium for maintaining the cells, comprising:

(1) a bioluminescent reagent comprising luciferin or a derivative thereof and a luciferase, said luciferin or derivative thereof emitting light in a bioluminescent reaction with the luciferase in the presence of ATP;

(2) a reagent which converts ADP to ATP; and (3) a buffer for reconstituted or diluting the bioluminescent and ADP-converting reagent, said components (1), (2) and (3) being present in proportions not exceeding those required to carry out a predetermined number of assays of the invention in an assay volume not exceeding 240 µl, provided that the buffer may be present in an excess of up to 80% by volume of its required proportion.

The term "assay" herein includes qualitative assesment, semi-quantitative measurement or assessment and quantitative measurement.

The terms "bioluminescent reagent" and "ADP-converting reagent" or equivalent include the plural, whenever the context permits.

FURTHER DESCRIPTION OF THE RELATED ART

It is known to use a combined assay of ATP and ADP, using a bioluminescence reaction. One first quickly measures the ATP in the sample, adds a reagent which converts ADP to ATP and takes a second light emission reading corresponding to the ADP concentration in the original sample. The ADP conversion results in a secondary increase in light emission. However, the signal stability so critical to the assay is lost at high ATP concentrations, for example, in excess of $10^{-6}$ molar (M), especially when the reaction is performed in a 1 ml volume see A. Lundin, PhD thesis: "Chemical applications of luminometric ATP monitoring", Karolinska Institute, Stockholm, (1990) and A. Lundin et al, Methods in Enzymology 133, 27–42 (1986), reproduced in the thesis. The problem is exacerbated dramatically when the reaction volume is less than 1 ml. Furthermore, eukaryotic cells contain approximately 100 times more ATP per cell than prokaryotic cells, making relative ATP and ADP concentration measurements in eukaryotic systems highly problematical.

One way of overcoming the problem of high ATP concentrations of $10^{-6}$M or more is to dilute the sample prior to ATP measurement. However, a major disadvantage of this approach is that, should the (unknown) ATP concentration of the sample be relatively low, dilution may extinguish the emitted light intensity which would have been observed, in which case it would be necessary to re-screen the sample. Clearly, the prospect of re-screening samples makes sample dilution an extremely unattractive approach for economic and practical reasons.

The present invention avoids or reduces these and other problems of the bioluminescent reaction.

DESCRIPTION OF THE PREFERRED EMBODIMENTS

Figure 1:
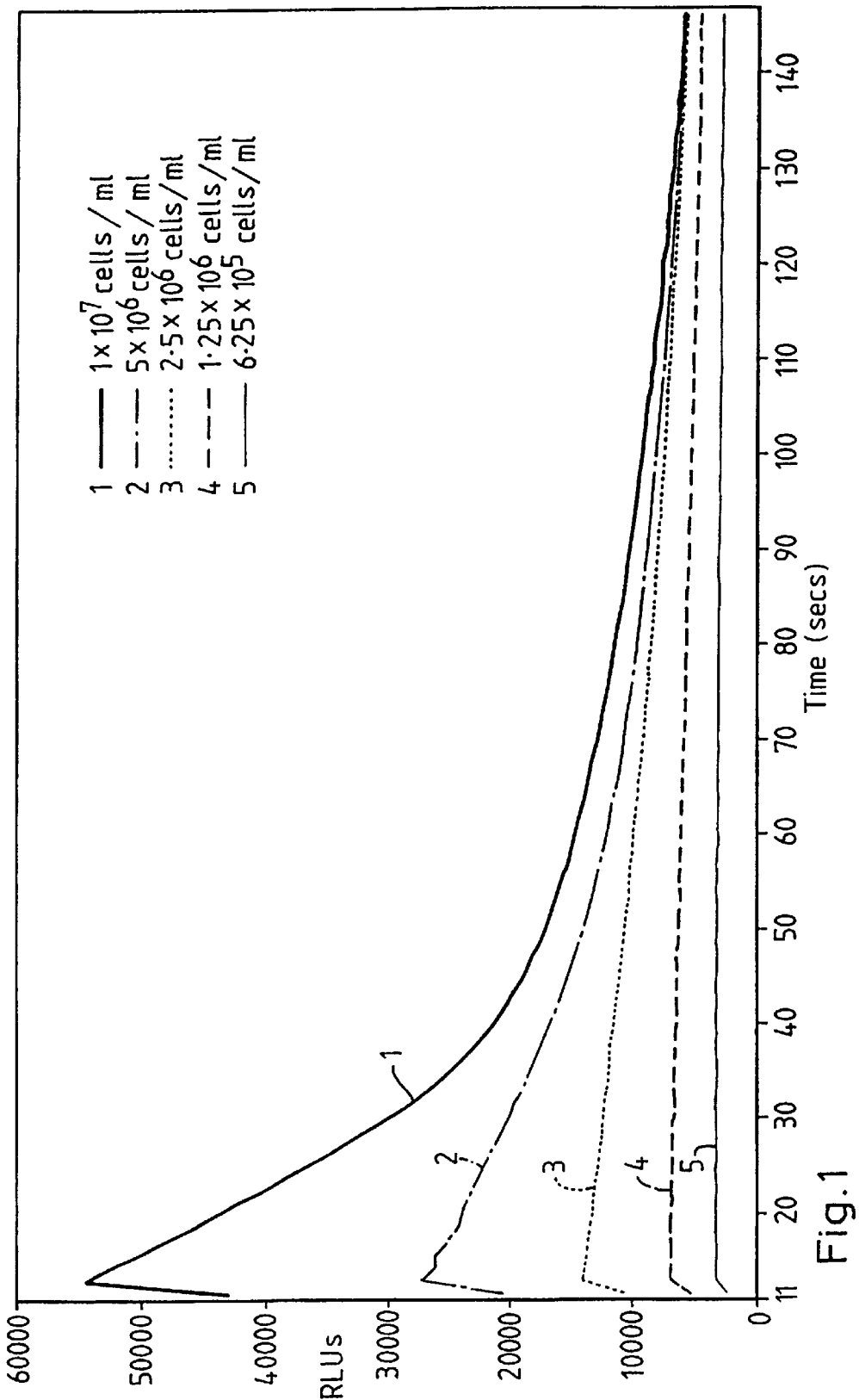
FIG. 1 is a plot of intensity of emitted light in relative light units on the y-axis against time in seconds on the x-axis for healthy cells subjected to the assay method of the invention. The cells are peripheral blood mononuclear cells and the cell densities range from $6.25 \times 10^5$ cells/ml up to $1 \times 10^7$ cells/ml.

The method of the invention is applicable to prokaryotic and eukaryotic cells. Prokaryotic cells generally require a more intensive adenylate nucleotide release procedure due to the presence of a cell wall and to the cell membrane constituents. Suitable such releasing reagents for prokaryotic cells include cationic detergents such as benzalkonium chloride, trichioroacetic acid (TCA) and dodecyl trimethylammonium bromide (DTAB). TCA and DTAB inhibit luciferase and would therefore require the sample to be treated with an agent such as cyclodextrin to "neutralise" the releasing agent. For eukaryotic cells, anionic or non-ionic release agents will normally be used, especially polyoxyethylene sorbitan fatty acid esters and polyoxyethylene ethers.

The method of the invention is particularly applicable to mammalian cell lines and mammalian primary cell cultures. Examples are given later.

The cells to be assayed can be a sample taken from a patient suffering from an illness resulting in a cellular abnormality. Thus, the invention is applicable to ex vivo diagnosis. (References herein to control cells should be understood in this context as meaning the corresponding normal cells taken from a patient who is not suffering from the illness). The invention is also applicable to cells of micro-organisms, insects and plants, for example. However, the main thrust of the invention is in assaying cells which have been treated with a candidate drug in screening. These cells will have been pre-incubated with the candidate drug, typically for a period of from 1 to 100 hours.

The determination of the condition of the cells is preferably relative, in the sense of distinguishing between different types of condition. The main use of the invention is in distinguishing between cells which have undergone apoptosis, cells which have undergone primary necrosis and proliferating cells. Cells which have undergone apoptosis can reach a necrotic condition, described as secondary necrosis. The text explains later how to distinguish secondary necrosis from apoptosis.

The releasing agent for releasing intracellular ADP and ATP, as described above, can be added to the cell sample separately or, more conveniently, along with the bioluminescent reagent.

The bioluminescent reagent can be any of the luciferin/luciferase general type. The active substrate is D-luciferin or a derivative thereof. U.S. Pat. No. 5,374,534 discloses D-luciferin derivatives which may be used with luciferase in the method of the invention.

Any other derivative can be used. The luciferase enzyme is preferably obtained naturally, especially from fireflies and most especially *Photinus pyralis*. However, the source of the luciferase is not critical, so long as it reacts with luciferin (or a derivative thereof) and ATP in the bioluminescent reaction. Examples are luciferases from *Luciola cruciata*, Diptera spp. and Coleoptera spp.

Synthetic, for example, recombinant luciferase can be used in the invention. It is described by Devine et al., Biochemica et Biophysica Acta 1173, No. 2, 121–132 (1993) and in European Patent 301,541 and U.S. Pat. No. 5,583,024.

An initial reading is taken of the intensity of emitted light after the beginning of the bioluminescent reaction, preferably immediately thereafter. This measurement represents the concentration of cellular ATP, designated A. It is also possible to measure the rate of change of light intensity as it decays, since the rate of decay is proportional to the initial ATP concentration, which can then be calculated and expressed as "A".

The normal kinetic course of the bioluminescent reaction, in the presence of cells which provide the necessary ATP for the reaction, is illustrated in FIG. 1 of the drawings. In FIG. 1, no ADP-converting agent has yet been added. Light intensity in relative light units (RLUs) is plotted against time in seconds. The first reading is after 11 seconds, representing the earliest time at which the equipment used could take a reading. At high cell (high ATP) concentrations, there is an initial surge of light, part only of which is shown in FIG. 1, because of the 11-second delay in taking the first reading, followed by a decay in the intensity of the emitted light. It will be seen that at lower concentrations the decay is extremely slight.

Shortly after 2 minutes, the light intensity has reached the desired substantially constant level of ATP, which forms a "baseline" for the next stage of the assay. In fact, the ATP present in the sample might be far more concentrated than FIG. 1 implies. The assay of the invention is intended to detect ATP in a concentration between femtomolar ($1\times10^{-15}$ M) and millimolar ($1\times10^{-3}$ M) and ADP in a concentration between picomolar ($1\times10^{-12}$ M). Thus, it will normally be advisable to wait longer than 2 minutes before adding the ADP-converting reagent. A preferred time range is 5 to 12 minutes, about 10 minutes being most preferred.

Figure 2:
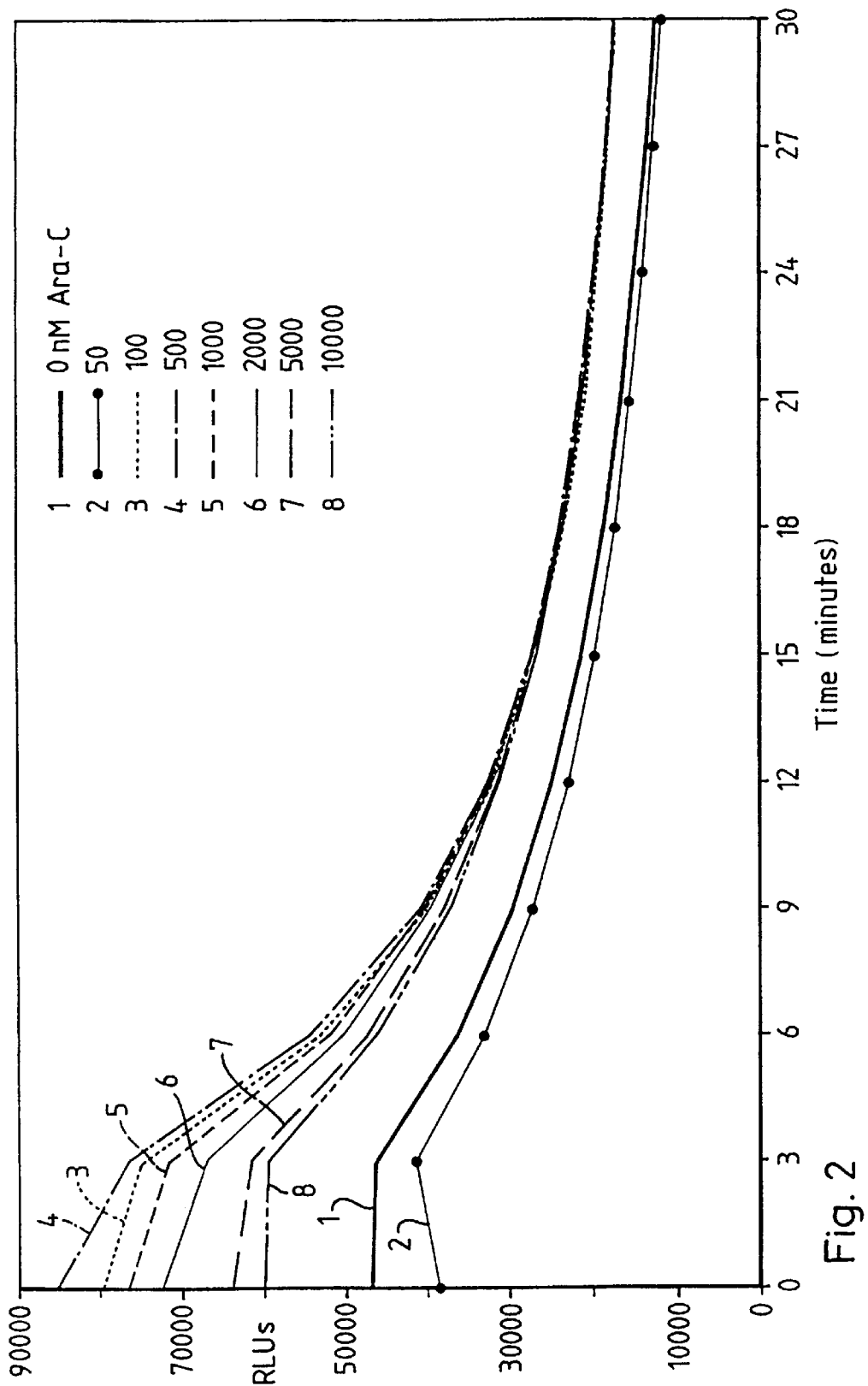
FIG. 2 is a plot similar to that of FIG. 1 except that the cells have been treated with the drug Ara-C, the luciferin-luciferase reagent used contained a high concentration of inhibitor, which resulted in a slower decay of the initial luminescence, and time is plotted in minutes;.

In certain unusual circumstances, it might be necessary to defer adding the ADP-converting reagent for as long as 30 minutes, a constant level of light not being reached until then. FIG. 2 illustrates this effect, which shows ATP decay using a non-preferred bioluminescent reagent, nucleotide releasing agent and various concentrations of Ara-C (arabinosylcytosine) in Jurkat cells.

Any ADP-converting reagent, which converts ADP into ATP, can be used, but preferably this reagent comprises the enzyme pyruvate kinase and phosphoenol pyruvate. Other ADP-converting reagents can be employed, for example adenylate kinase, glycerol kinase, myokinase and a combination of creatine kinase and creatine phosphate.

At around this time, when the level of intensity of emitted light is reasonably constant, and the ADP-converting reagent has just been added, is added or is about to be added, a reading, B, of the intensity of emitted light is taken. This serves as the "baseline" reading for the determination of ADP concentration.

Initially in the assay, it is desired to have the emitted light intensity decay as rapidly as possible. When, after the decay, the intensity becomes substantially constant and the ADP-converting reagent is added, it becomes once more desirable to attain a new substantially constant or plateau level,. in order to give a steady reading of light intensity, "C". The bioluminescent reagents available commercially contain inhibitors of the luciferin-luciferase reaction, such as L-luciferin and inorganic pyrophosphate. These reagents are helpful in conventional bioluminescent assays, as they produce a prolonged "glow", rather than a rapid decay. However, this is the very antithesis of what is required in the present invention. Preferably, therefore, the bioluminescent reagent is formulated to have a reduced or zero content of inhibitor. Omitting the pyrophosphate is particularly desirable. On the other hand, it becomes preferable to generate a prolonged glow after addition of the ADP-converting reagent, in order to ensure that sufficient bioluminescent reagent remains to react with all the ATP converted from the ADP. Preferably, therefore, an inhibitor of the reaction is added with, or at about the same time as, the ADP-converting reagent. For example, pyrophosphate could be added at this point.

ADP concentration is measured by taking a subsequent reading of the light intensity at level "C", and then subtracting "B" from "C". The time of talking reading "C" is dependent on ensuring adequate conversion of the ADP. Ordinarily, the light level will reach a plateau. If the cells are viable the light intensity will not increase significantly from "B" to "C". Indeed, in a few cases, particularly when the growth of the cells has become arrested in their G2/M phase, it will actually fall. C–B will then be negative. If the cells are in an apoptotic or necrotic condition; however, C will be greater than B. Since a principal aim of the assay is to detect apoptosis and necrosis, the point C could be defined by reference to producing a significant difference C–B for such cells. Otherwise C can be defined as on a plateau of light output, this plateau being a new substantially constant level. Preferably C is taken from 1 to 20 minutes after addition of the ADP-converting reagent, more preferably 2 to 8 minutes and most preferably at about 5 minutes. Taking the reading at about 5 minutes is particularly useful when microtitre plates are being scanned in many conventional luminometers reading B can be taken for all wells can be taken before reading C commences. At high ADP concentrations a plateau is reached after 1 minute, but at low concentrations after 20 minutes.

Figure 3:
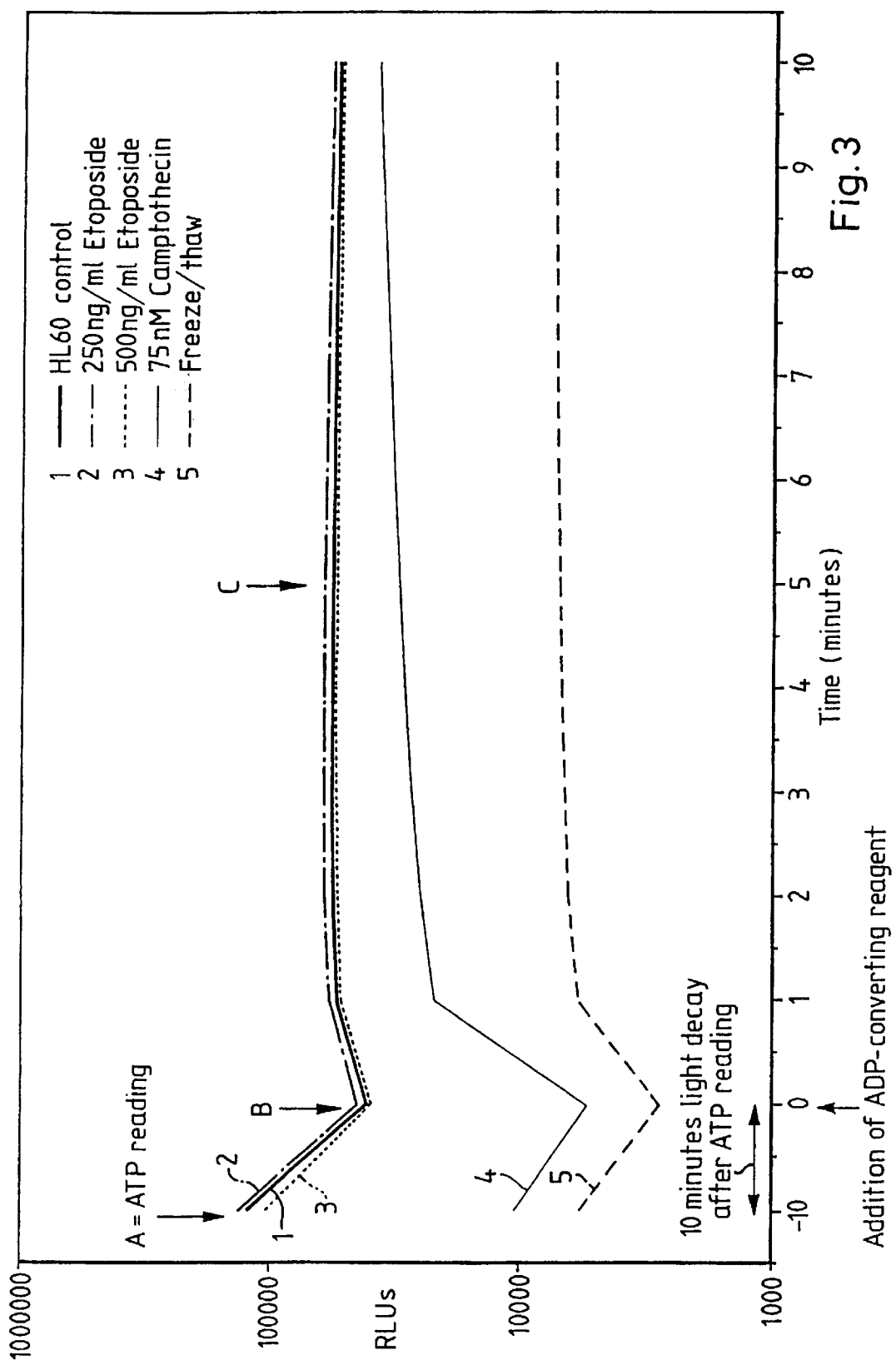
FIG. 3 is a plot of intensity of emitted light in relative light units on the y-axis against time in minutes on the x-axis in an assay method of the invention (Example 1) and shows the data points A, B and C in a typical determination of the ADP to ATP ratio.

FIG. 3 of the drawings illustrates the various stages of a the assay of the invention of Example 1 for cells treated with various concentrations of etoposide and shows the times at which readings A, B and C are most preferably taken.

The bioluminescent reagent is added to the cell sample in the luminometer at time −10 minutes. There is a 10 minute lag period prior to addition of the ADP-converting reagent at time 0, this gives another light intensity reading at point B on the figure, i.e. the ATP reading at the time of the beginning of the converision of ADP to ATP. If there is ADP present there will be an increase in light output as the ADP is converted to ATP and interacts with the luciferin/luciferase. This light output begins to plateau depending on how much ADP is present. Reading C is taken after 5 minutes. The difference between B and C correlates with the amount of ADP present in the reaction mixture. This difference can then be related back to the original ATP reading A as a ratio:

$$ADP{:}ATP = (C-B){:}A, \text{ alternatively written } (C-B)/A$$

This ratio is the preferred method of relating (C–B) to A. As a cell becomes increasingly metabolically challenged, its ability to generate ATP falls below its rate of consumption, and therefore the ADP concentration, increases in relation to the ATP concentration and ADP/ATP ratio increases. The invention is able to detect these changes and use the values of ADP and ATP to determine the degree of apoptosis or necrosis that has occurred in a culture. Substantially no increase in the ratio indicates healthy or proliferating cells.

It will be appreciated that A, B and C are best taken at time "points", by integrating the light output over 100 milliseconds, but that they could be taken by integrating over a longer time. Also, the ratio (C–B): A can be inverted, expressed as adenylate energy change, which also involves measurement of AMP or determined from a calibrated assay in which relative light units are converted to absolute light units. Also, (C–B) could be determined in a separate assay from A.

The assay of the invention is conveniently used to determine the condition of cells as falling into one of three categories:

(1) Proliferating cells or those having a substantially constant number of viable cells. The former includes healthy cells and cells which have been induced to proliferate. The latter includes such conditions as cells in which there is a steady state between production of new cells and decay of old ones and cells whose growth has been arrested in the G2/M phase, the cells having doubled their content of DNA and being ready, but unable to divide.

(2) Cells undergoing apoptosis or secondary necrosis, which is a necrotic cell death after apoptosis; and (3) Cells undergoing primary necrosis.

When the ATP concentration is expressed by the light intensity A immediately after the start of the bioluminescent reaction, an indication of cell condition, valid in most instances, is as follows:

| (C − B): A | Corresponding condition of cells |
|---|---|
| Negative or substantially zero | (1) |
| Substantially zero up to 2 (more usually up to 1.5) | (2) |
| Above 2 | (3) |

In order to distinguish the condition of cells having a small, positive (C−B):A ratio, it will sometimes be desirable to compare the (C−B):A ratio of the sample cells with that of control cells. Thus, the term "substantially zero" is conveniently and preferably interpreted as the same as corresponding normal control cells or within 10% thereof, more preferably within 5% thereof. Indeed, more generally, the difference between (C−B):A for sample and control is another way of relating (C−B) and A readings to the condition of cells.

The above numerical ranges will suffice in most cases, but, strictly, this is not the most helpful way of determining cell condition. Most desirably, the assay is standardised for the particular kind of cells used. This may be done by treating the cells to impart to them a particular condition and assaying these cells by the method of the invention and by a different method and comparing the results. Preferably, the ratio (C−B):A from the method of the invention is compared with the condition of the cells determined by the second method. Values of the (C−B):A ratio can then be set accordingly. The ratio can then be re-expressed as % apoptosis or % necrosis, when this is useful. The different method used in the standardisation can be any which gives an accurate result. It can be a conventional method such as the PI or TUNEL method with flow cytometry, referred to above. These methods are described in many books and papers, for example in "Techniques in Apoptosis: A User's Guide", Ed. T. G. Cotter and S. J. Martin, Portland Press. London (1996). However, other usable, slow but accurate methods might be found in the future. It will be appreciated that the method of the present invention gives a high throughput and its advantages are not significantly diminished by having to standardise it occasionally against a lower throughout method.

The chief aim of the invention is to distinguish apoptotic, necrotic and fully viable cells. However, various refinements can be added to determine other cell conditions. Thus, in one embodiment, the method further comprises distinguishing growth-arrested cells in G2/M phase of the cell cycle from proliferating or control cells by the higher ATP level represented by light intensity measurement A in the growth-arrested cells, and by a lower ADP:ATP ratio represented by (C−B):A in the growth-arrested cells. In another embodiment, the method further comprises carrying out the assay without nucleotide-releasing step (a) and distinguishing secondary necrosis from apoptosis by the higher ADP level represented by light intensity measurement difference C−B in the necrotic cells when the nucleotide-releasing step is omitted. Other ways of making this distinction are described in the Examples, but are of general applicability to the invention.

A fundamental advantage of the invention is that it can be carried out in small assay volumes. The term "assay volume" means the total volume of liquid in which the assay is carried out (including, of course, the volume of the ADP-converting reagent) added during the assay. The invention has been made particularly for use with 96-well microtitre plates (microplates) in which the wells are filled to (say) not more than 240 µl and preferably not more than 220 µl. However, the invention could be used with microtitre plates having even smaller wells, requiring smaller assay volumes. In these small assay volumes, the sample volume is very large in relation to assay volume, e.g. 100 µl out of 220 µl. In other words, the ATP concentration will often be very high. This is the nub of the problem prior to this invention, because it was thought necessary to carry out the assay in very large assay volumes, of about 1 ml. Large volumes were thought necessary to dilute the ATP, to avoid the problem of an unstable initial light level. While dilution overcomes this particular aspect of the problem, it means that the assay cannot be carried out in a microtitre plate. It also means that the concentration of ADP in the prior assay will be very low, so that the difference in ATP levels before and after adding the ADP-converting reagent will be liable to inaccuracy, being a difference between two relatively small numbers.

The growth of cells in culture can be very unpredictable; cell numbers can be very high or very low. Since the goal is to determine the effect of a new drug on viable cell numbers, it is essential that the testing method has a very wide dynamic range. The demands of high throughput screening dictate that the maximum number of results must be within the measurable range of the test method. It becomes very expensive to repeat trials when data is outside specifications. The invention allows ATP and ADP to be measured at concentrations which were previously not possible in the microtitre plates without the need for dilution. These levels are equivalent to the levels routinely encountered in high throughput screening and therefore the invention allows bioluminescerit technology to enter a completely new field of application. The invention further includes a kit for carrying out an assay of the physical condition of a sample of biological cells in vitro, in a medium for maintaining the cells, comprising:

(1) a bioluminescent reagent comprising luciferin or a derivative thereof and a luciferase, said luciferin or derivative thereof emitting light in a bioluminescent reaction with the luciferase in the presence of ATP;

(2) a reagent or reagents which converts cellular ADP to ATP; and (3) buffer for reconstituting, diluting, or dissolving (as the case may be) the bioluminescent and ADP-converting reagents, said components (1), (2) and (3) being present in proportions not exceeding those required to carry out a predetermined number of assays, each in an assay volume not exceeding 240 µl, provided that the buffer may be present in the kit in an excess of up to 80% by volume of the proportion required for the assay. Preferably the buffer does not exceed 50% by volume of its required proportion. The bioluminescent reagent is preferably supplied with the luciferin (or derivative thereof) and the luciferase in a single container, for convenience, although they could be provided in separate containers if desired. The ADP-converting reagent is preferably supplied separately from the bioluminescent reagent. Both can be supplied in a freeze-dried form for reconstitution with buffer, as a stable stock solution, or formulated with an inert solid carrier as tablets, for dissolution in the buffer. In either case, they need to be made up with buffer before use in the assay.

The amount of buffer provided in a third container should be sufficient for this purpose and provide some excess to compensate for error or wastage by the user. However, these reagents can alternatively be supplied made up with buffer, ready to use. It will be appreciated that when the assay of the invention is conducted in a small volume, e.g. up to 240 μl, the amount of buffer required for each assay will be a great deal less than used by A. Lundin, supra, in his assay conducted at a volume of about 1 ml, thus distinguishing the kit of the present invention from the reagents used by A. Lundin. Preferably the bioluminescent and ADP-converting reagents are provided in the form of a number of separate measured doses, each dose being the amount required for one assay. These doses are preferably contained in 10 ml vials.

The present invention also provides a PEP/PK reagent which comprises from 1.7 to 50 mM PEP and 8.3 to 250 U/ml. PK, based on the reagent immediately before it is added to the wells. Preferably the ratio of units of PK to micromoles of PEP is from 2:1 to 8:1, more preferably 3:1 to 6:1 and most preferably about 5:1.

The reagents used by A. Lundin at pages 37–38 of the 1986 paper cited supra, include 10 μl of ADP-converting reagent prepared by mixing equal volumes of 0.2M phosphoenolpyruvate (PEP) and pyruvate kinase (PK) (10 mg/ml). Thus, the PEP concentration is 0.1M and the PK concentration is 5 mg/ml. Assuming that the Boehringer-Mannheim PK contained 200 U/mg, this appears to be a concentration of 1000 U/ml. Thus, the PK:PEP ratio of Lundin is about 10 U PK: 1 μM PEP. The advantage of the lower concentration of PK and lower PK:PEP ratio in the present invention is that the ADP to ATP conversion does not take place excessively quickly.

The invention includes the new PEP/PK reagent, having a ratio of units of PK to micromoles of PEP from 2:1 to 8: 1, per se. Another new PEP/PK reagent is characterised in that it further comprises an inhibitor which will delay the bioluminescent reaction, as explained above, e.g. pyrophosphate. The invention also includes an assay kit for carrying out an assay of the physical condition of a sample of biological cells in vitro, in a medium for maintaining the cells, comprising:

(1) a bioluminescent reagent comprising luciferin or a derivative thereof and a luciferase, said luciferin or derivative thereof emitting light in a bioluminescent reaction with the luciferase in the presence of ATP; and (2) either of the new PEP/PK reagents defined above, regardless of whether the above-mentioned buffer component is included in the kit or not.

Preferably the kit includes a holder comprising a plurality of wells in which the assay can be carried out in an assay volume of 240 μl or less, especially a microtitre plate.

It can further comprise a reagent for releasing intracellular adenylate nucleotides from the cells of the sample. It can also comprise a light detector such as a luminometer or scintillation counter which is preferably portable. The luminometer is preferably a known microplate luminometer such as "LUCY 1" from Anthos, Austria or "LUMINOSKAN" from Lab Systems Oy, Helsinki, Finland.

ATP and ADP standards may be provided as freeze-dried preparations for reconstitution before use. Since they need to be stored at about −20° C., it is possible, but not very convenient, to supply them integrally with the other components of the kit, which can be stored at 4° C.

The study of death of a particular cell type is useful in testing candidate drugs for a variety of conditions including cancers, Alzheimer's Disease, HIV & AIDS and Diabetes. It can be used in toxicity testing, e.g. of cosmetic and personal care compounds. Another use is to test the cells of organisms present in environmental samples, such as factory effluent which is released into rivers, and plant and insect cells, where pollution is suspected, e.g. by herbicides or pesticides.

Further uses include testing human cells from biopsies, e.g. to detect metabolic changes in tumours, pancreatic cells, heart muscle cells or damage to liver cells. The viability of spermatozoa before in vitro fertilisation can be tested by this method.

Another area of use is in testing plant cells in germination assays in vitro, e.g: for maize pollen.

The following Examples illustrate the invention.

EXAMPLES

Reagents:

Bioluminescent (Luciferin/Luciferase) reagent. This was supplied by Bio-Orbit OY, Turku, Finland as a freeze dried powder to be be reconstituted prior to use. The powder contains luciferase from *Photinus pyralis* (40 μg), Luciferin (42 μg: believed to contain 96% D-Luciferin; 4% L-Luciferin), bovine serum albumin (50 mg), magnesium sulphate (1.23 mg) and inorganic pyrophosphate (0.446 μg). It was reconstituted to 10 ml of 0.1 M Tris-acetate buffer, pH 7.75 containing 2mM EDTA (dipotassium salt).

Nucleotide-releasing agent. 0.1 M Tris acetate buffer pH 7.75 containing 2 mM EDTA (dipotassum salt), 0.25% v/v Triton X-100 and 1 μM dithiothreitol.

ADP-converting reagent. This was prepared by mixing equal volumes of 2 M potassium acetate, 500 units/ml pyruvate kinase (PK) and 100 mM phosphoenol pyruvate (PEP). An equal volume of Tris-acetate buffer pH 7.75 was then added. The PK and PEP were thus diluted 1:6 when the converting reagent was made up from the stock solutions. Since 20 μl of converting reagent is present in 220 μl of the sample and other reagents in the wells, the PK and PEP were further diluted 1:11 in the wells. The concentrations of this reagent in the wells were 30 mM potassium acetate, 7.6 units/ml pyruvate kinase and 1.5 mM phosphoenol pyruvate.

Commercial preparations of pyruvate kinase contain high levels of ATP and ammonium sulphate which is inhibitory to luciferase. Such preparations should be dialysed extensively against a suitable buffer, e.g. Tris-acetate buffer before use. A glycerol preparation, free of ammonium sulphate, is very useful.

Cell lines tested

TF-1, Human erythroleukaemia.

K562, Human Chronic Myeloid Leukaemia in blast crisis.

HL-60, Human Acute Promyelocytic Leukaemia.

CEM-7, Human T Lymphoblastic Leukaemia.

JURKAT, Human T Lymphoblastic Leukaemia.

CHO, Chinese Hamster Ovary.

Daudi, Human Burkitt Lymphoma.

B-9, Mouse IL-6 Dependent.

PC-1 2, Human Nerve Growth Factor-dependent Neuronal.

L-929. Mouse Fibroblast.

NFS-60, Mouse Myeloid.

NIH 889, NIH 526 and NIH 841, Human Small Cell Lung Cancer.

Molt-4, Human T Lymphoblast.

H-36, Human Lens.

U-937, Human histiocytic (a lymphoma cell line with monocytic features)

Primary Cultures

Human Peripheral Blood Mononuclear Cells.

Human Peripheral Blood Polymorphonuclear (neutrophil) Cells.

Human Acute Myeloid Leukaemia ("AML") Blast Cells.

Airway Smooth Muscle Cells from Bovine Trachea.

The above cell lines are commercially available from Sigma Biosciences a division of Sigma Chemical Co., Sigma-Aldrich Co. Ltd. And/or the European Collection of Cell Cultures, CAMR, Salisbury, Wiltshire, United Kingdom and Clonetics (distributed by BioWhittaker) Wokingham, UK.

Methods of assay

Method 1

Cell lines or primary cell cultures of interest were cultured in conventional transparent tissue culture microplates or white walled, clear bottomed tissue culture microplates in a suitable cell culture medium (e.g. RPMI 1640 supplemented with Foetal Calf Serum) after treatment with a drug under test or treatment in some other way under investigation. Untreated control cell cultures were also included in the wells of the plate. The microtitre plates were loaded into the luminometer. The assay was performed after a suitable culture period varied according to the treatment and type of cells.

After the culture period. 100 µl of the nucleotide releasing buffer was added to all the wells of the microtitre plate. The samples were incubated at room temperature for 5 minutes.

The microtitre plate was then loaded into the luminometer which was programmed to automatically add 20 µl of luciferin/luciferase reagent and take a measurement for each well. The first such measurement was designated "A". Following a 10 minutes waiting period, i.e. sufficient time to allow for the signal to decay to a substantially constant level, a second reading ("B") was taken. The luminometer then added 20 µl of ADP-converting reagent to each well and read each well every minute for a 10 minute period. (The readings taken over 10 minutes were to confirm the reaction kinetics: a single reading taken after 5 minutes was actually used as the reading "C".)

The reading ("B") taken immediately after addition of the ADP converting reagent and the reading "C" taken after 5 minutes addition of this reagent were then used to calculate the ADP/ATP ratio, (C−B):A, used to differentiate between apoptosis and necrosis.

The cells may be cultured either in transparent tissue culture microplates or in white walled microplates with clear bases. If the former are used, the nucleotide extract is preferably transferred to white microplates before taking measurements in the luminometer.

Method 2

This method was the same as in Example 1 except as follows. The luciferin/luciferase reagent and nucleotide-releasing reagent were mixed and thus added together. In this method the luciferin/luciferase reagent was reconstituted in 50 ml of the nucleotide-releasing agent before use. The luminometer added 100 µl of this combination reagent. The readings were taken as in Example 1.

Example 1

This Example illustrates how the assay of the invention can be used to recognise various types of cell condition. HL60 cells were incubated for 24 hours with two different concentrations of anti-cancer drugs etoposide and camptothecin or were freeze-thawed by leaving them for 15 minutes at the temperature of liquid nitrogen and warming them up to 37° C. Method 2 was used for the assay. Results are shown in Table 1.

TABLE 1

| Treatment | A | B | C | (C − B) | Ratio (C − B)/A | Conclusion |
|---|---|---|---|---|---|---|
| Control | 120333 | 40855 | 56472 | 15617 | 0.13 | Proliferation |
| 250 ng/ml etoposide | 131478 | 44443 | 60653 | 16210 | 0.12 | Growth arrest |
| 500 ng/ml etoposide | 1593 | 3722 | 8201 | 4409 | 0.58 | Apoptosis |
| 75 nM camptothecin | 5738 | 2788 | 6967 | 4179 | 0.73 | Secondary necrosis |
| Freeze/thaw | 10375 | 5355 | 30724 | 25369 | 2.45 | Primary necrosis |

With 250 ng/ml$^{-1}$ of etoposide the ADP:ATP ratio was positive, but lower than control. There was a slight increase in the ATP reading at A. This was not related to proliferation, but indicated an increase in cell size due to growth arrest in cell cycle phase G2/M (confirmed by PI staining). Etoposide used at 500 ng/ml gave an ADP:ATP ratio of 0.58, indicating apoptosis. Secondary necrosis (as a result of the cells having initially undergone apoptosis) was seen with 75 nM camptothecin. The ADP:ATP ratio was again positive (0.73), but ATP and ADP levels were even lower than for primary necrosis. Freeze-thawing the cells caused damage and induced primary necrosis. In this case there was a dramatic drop in the ATP levels and a marked rise in ADP levels, giving a very high ADP:ATP ratio.

Figure 4:
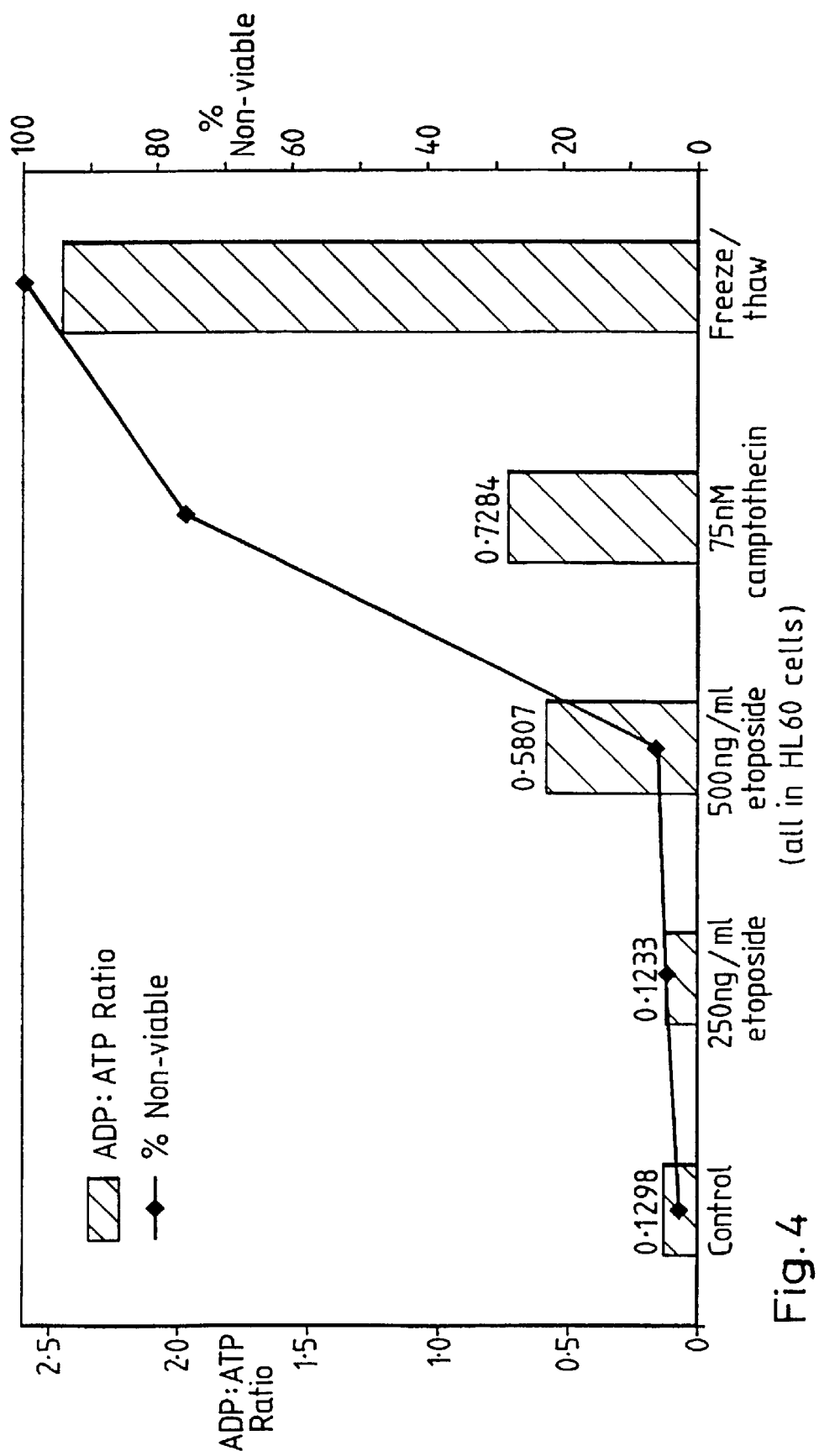
FIG. 4 illustrates the correlation for the data of FIG. 3 with cell viability using the PI uptake method and drugs and concentrations thereof selected to illustrate various different conditions of the cells.

On the basis of ADP:ATP ratios above it is difficult to distinguish apoptosis from secondary necrosis. One pointer is the exceptionally low levels of ATP, which ate even lower in secondary necrosis than in apoptosis. Another means of distinguishing is to repeat the assay omitting the nucleotide-releasing agent, as described above. A third way is to standardise the assay against another method of assay which will distinguish necrotic cells from others. This is illustrated in FIG. 4 of the drawings (bar chart), which compares the ADP:ATP ratios in this Example with the percentage of non-viable cells, as determined by propidium iodide uptake and flow cytometry (line). (Uptake of PI denotes that the cells are leaky and is a measure of cell viability. This should not be confused with PI staining of cells which have been made permeable, as a means of measuring apoptosis.)

Example 2

Using Method 2 above on CEM7 cells incubated for 48 hours with various concentrations of dexamethasone, ADP:ATP ratios were determined as the ratio (C−B):A. The ratio increased from 0.24 at 50 nM dexamethasone to 0.77 at 750 nM, indicating an increasing degree of apoptosis.

Figure 5:
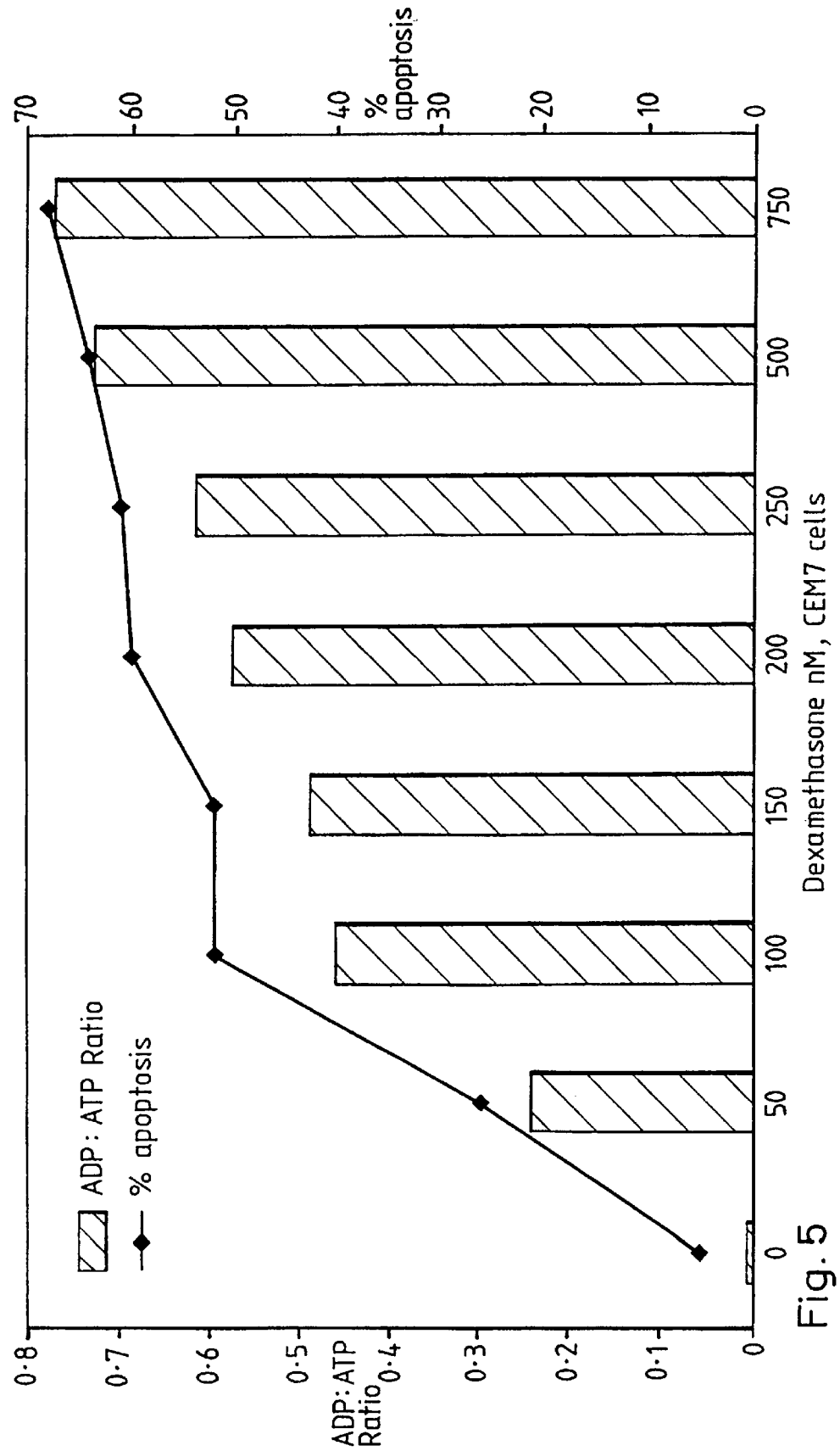
FIGS. 5 and 6 are plots which compare the percentage apoptosis or necrosis as determined by the conventional propidium iodide (PI) or TUNEL method, respectively, (line) with the ADP/ATP ratio as determined by the method of the invention (bar chart) for increasing concentrations of the apoptosis-inducing drugs dexamethasone on the cell line CEM7 (FIG. 5) and camptothecin on the cell line HL60 (FIG. 6).

The assay was standardised using PI staining with flow cytometry, to measure apoptosis. The results are shown in FIG. 5, where the bar chart denotes the ADP:ATP ratio measurements from the present invention and the line through the plot points denotes % apoptosis determined by PI. The correlation was excellent.

Once the assay of the invention has been standardised once, in this or another way, for the kind of cells being used, it can be used for the high throughput screening of the same cells, incubated with candidate drugs.

Example 3

Using Method 2 above on HL60 cells incubated for 24 hours with various concentrations of camptothecin, ADP:ATP ratios were determined as the ratio (C−B):A. The ratio increased from 0.14 at 50nM camptothecin to values between 0.47 and 0.50 at 300 nM or above, indicating an increasing degree of apoptosis.

Figure 6:
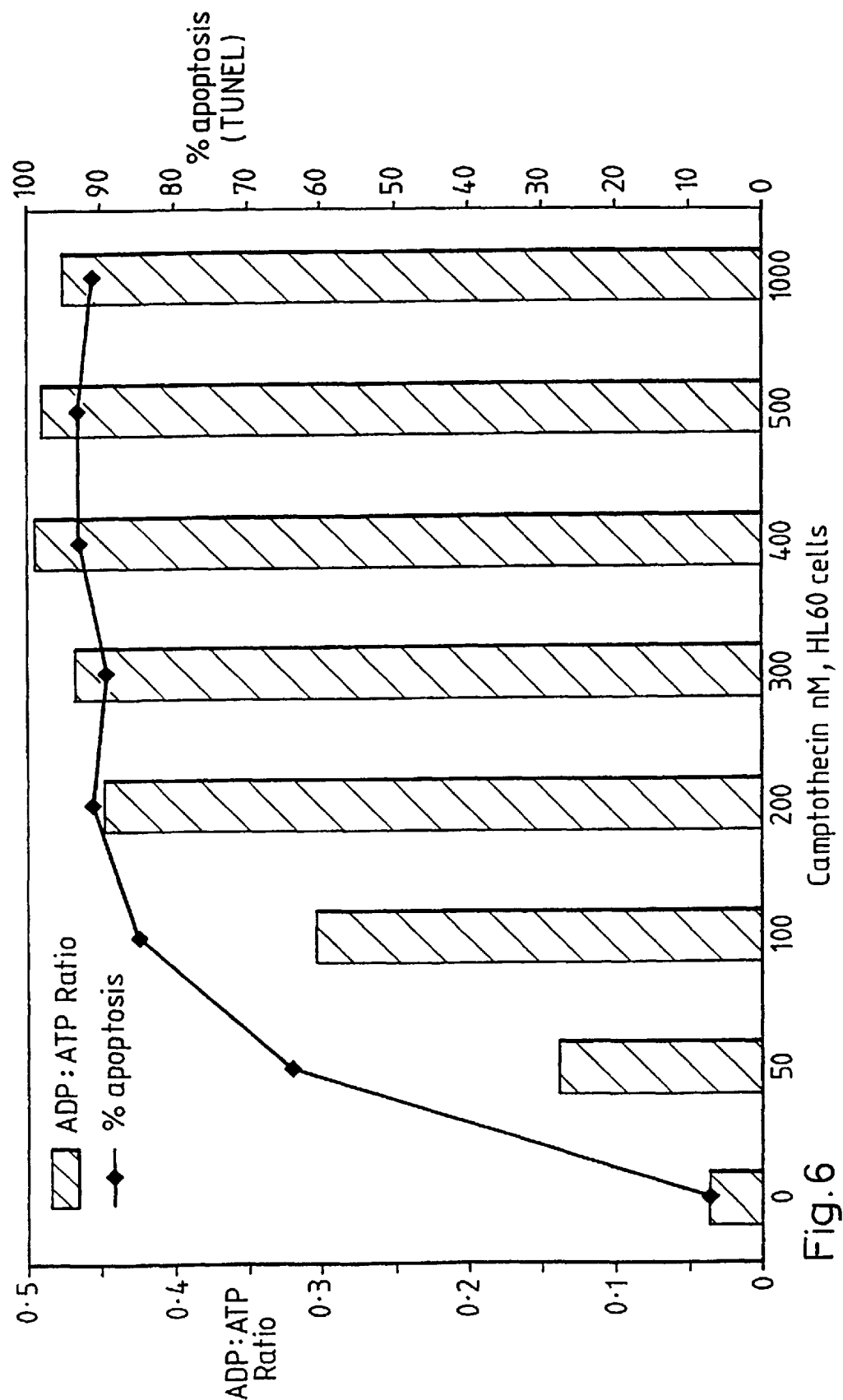

The assay was standardised using the TUNEL method with flow cytometry to measure apoptosis. The results are shown in FIG. 6, where the bar chart denotes the ADP:ATP ratio measurements from the present invention and the line through the plot points % apoptosis determined by TUNEL. The correlation was good, showing that the assay can be standardised in this way.

Example 4

Various cell lines were incubated with a range of drug concentrations that induced varying degrees of apoptosis. These drug concentrations varied according to the agent used. The incubation time also varied according to the type of drug, from 24 to 72 hours prior to determination of apoptosis. At the end of the culture period the assay of the invention was carried out and percentage apoptosis was confirmed using propidium iodide staining and flow cytometry.

Some cell lines will not proliferate in culture in the absence of an additional factor. Examples of these cells include TF-1 cells which require Granulocyte-Macrophage Colony-Stimulating Factor, PC-12 cells which require Nerve Growth Factor and B-9 cells which require interleukin-6. Withdrawal of these factors or the presence of sub-optimal concentrations thereof results in apoptosis. Cells were cultured in the absence (or at reduced concentrations) of growth factor for 24 or 36 hours, as indicated.

Neutrophils, isolated from the blood of normal healthy subjects, were incubated in culture medium containing foetal calf serum (FCS). The cells will remain viable for approximately 24 hours under these conditions. However, when FCS was removed from the culture medium, the neutrophils underwent apoptosis.

Necrosis can be induced by mechanical means, which include repeated freeze-thawing which affects the membrane integrity of the cells. Heating the cells affects many of the biochemical processes vital for cell viability and again a rapid induction of necrosis occurs. Certain cells will tolerate these treatments better than others. For example, when K-562 cells were heated at 56° C. for 30 minutes, not all the cells were induced to undergo necrosis.

Throughout, Method 2 was used, except for PC-12 and the neutrophils where Method 1 was used. (Method 1 is better for adherent cells). For each type of treatment control samples were set up, where the cells were incubated in the control medium in the absence of drug or other treatment. Results are shown in Table 2 below. The % apoptosis was determined by PI staining with flow cytometry and % necrosis by acridine orange/ethidium bromide staining.

TABLE 2

| Cell type | Treatment and period of incubation | Control cells $\frac{C-B}{A}$ | % Apo/Nec | Treated cells $\frac{C-B}{A}$ | % Apo/Nec |
|---|---|---|---|---|---|
| CEM-7 | 50 nM Dexamethasone, 72 h. | 0.06 | 5 | 0.31 | 40 |
| CEM-7 | 500 nM Dexamethasone, 72 h. | 0.06 | 5 | 0.42 | 67 |
| CEM-7 | 1000 ng/ml Etoposide, 72 h. | 0.31 | 3 | 0.51 | 55 |
| HL-60 | 100 nM Camptothecin, 24 h. | 0.16 | 5 | 0.48 | 52 |
| HL-60 | 500 nM Camptothecin | 0.16 | 5 | 0.73 | 70 |
| HL-60 | 1000 ng/ml Etoposide, 24 h. | 0.22 | 5 | 0.35 | 56 |
| HL-60 | 5000 nM Ara-C, 24 h. | 0.09 | 7 | 0.15 | 43 |
| TF-1 | GM-CSF withdrawal, 24 h. | 0.09 | 18 | 0.12 | 42 |
| PC-12 | NGF withdrawal, 36 h. | 0.52 | 8 | 3.23 | 46* |
| B-9 | IL-6 withdrawal, 24 h. | 0.25 | 20 | 0.52 | 47 |
| U-937 | 200 nM Camptothecin, 24 h. | 0.02 | 5 | 0.24 | 40 |
| AML | 10 mM Ara-C, 48 h. | 0.11 | 16 | 0.45 | 62 |
| Neutrophils | FCS withdrawal, 24 h. | 0.36 | 16 | 0.44 | 23 |
| CEM-7 | LN2, 15 min., Freeze-thaw | 0.26 | 18 | 3.71 | 100* |
| HL-60 | LN2, 15 min., Freeze-thaw | 0.13 | 10 | 2.44 | 100* |
| Jurkat | LN2, 15 min., Freeze-thaw | 0.23 | 14 | 2.79 | 100* |
| K562 | Heat treatment (56° C.), 30 mins 30 mins | 0.10 | 10 | 8.86 | 100* |

*primary necrosis

Key GM-CSF, Granulocyte-Macrophage Colony-Stimulating: NGF, Nerve Growth Factor: IL-6, Interleukin-6: AML, Acute Myeloid Leukaemia blast cells: FCS, Foetal Calf Serum: LN2, Liquid nitrogen.

Example 5

Using Method 2 above on CEM7 cells incubated for 48 hours with various concentrations of etoposide, ADP:ATP ratios were determined as the ratio (C−B):A. The assay was standardised using PI staining with flow cytometry, to measure apoptosis.

The results, shown in Table 3 below, show how cells growth-arrested in the GM/2 phase can be detected. At 250 and 500 ng/ml etoposide, the ADP:ATP ratio is substantially zero (being less than control). However, the ATP concentration, as determined from reading A, has increased slightly. (That the increase in the ATP is real can be verified by a cell count. The control cell count was $1.6 \times 10^6$/ml, but at 250 and 500 ng/ml etoposide it was $0.3 \times 10^6$/ml. The growth-arrested cells are much bigger, containing double the usual amount of DNA.) At 1000 ng/ml etoposide, the cell condition is clearly apoptotic as there is an increase in ADP:ATP ratio such that it may be considered positive. The degree of apoptosis increases at higher concentrations of etoposide. The 750 ng/ml reading represents a "difficult case", where the cells are in an intermediate condition between growth-arrested and apoptotic.

TABLE 3

| Conc. of etoposide (ng/ml) | A | $\frac{C-B}{A}$ | % apoptosis (by PI) | Cell condition |
|---|---|---|---|---|
|  | 2,015,379 | 0.041 | 1 | Control |
| 250 | 2,096,871 | 0.025 | 6 | Growth arrested |
| 500 | 2,152,420 | 0.025 | 5 | Growth arrested |
| 750 | 1,969,406 | 0.028 | 11 | (see text) |
| 1000 | 1,440,587 | 0.065 | 18 | Apoptotic |
| 1500 | 1,341,493 | 0.072 | 42 | Apoptotic |
| 2000 | 532,213 | 0.097 | 61 | Apoptotic |
| 3000 | 487,318 | 0.094 | 65 | Apoptotic |

We claim:

1. A method of assay of the physical condition of a sample of biological cells in vitro, in a medium for maintaining the cells, comprising:
   (a) adding to the sample an agent which releases adenylate nucleotides from the interior of the cells to be assayed into the medium containing the cells;
   (b) simultaneously or subsequently adding to the sample a bioluminescent reagent comprising luciferin or a derivative thereof and a luciferase, said luciferin or derivative thereof emitting light in a bioluminescent reaction with the luciferase in the presence of ATP;
   (c) after said addition, measuring the intensity of the emitted light or its change with respect to time elapsed, to determine an ATP concentration;
   (d) after the initial light intensity has reached a substantially constant level, adding a reagent which converts cellular ADP to ATP;
   (e) using light emitted thereafter or its change with respect to time elapsed to determine and ADP concentration; an
   (f) using information from the ADP and ATP concentrations thus determined to determine the physical condition of the cells.

2. The method according to claim 1, wherein the ATP concentration is determined by measuring the intensity of light immediately after addition of the bioluminescent reagent and the ADP concentration is determined by measuring the intensity of light at about the same time as the ADP-converting reagent is added.

3. The method according to claim 1 wherein in step (f) an ADP:ATP ratio is determined and is used to determine the physical condition of the cells.

4. The method according to claim 3, wherein the assay is standardised by treating the corresponding normal cells to impart to them a particular condition and assaying these cells by (1) a method as defined in said claim and (2) a different method, comparing the ADP:ATP ratio obtained in method (1) with the condition of the cells as determined by method (2) and setting values of this ratio accordingly, for use in the method defined in said claim.

5. The method according to claim 1, wherein in step (f) information is used to distinguish between cells which have undergone apoptosis, cells which have undergone primary necrosis, and proliferating cells.

6. A method of assay of the physical condition of a sample of biological cells in vitro, in a medium for maintaining the cells, comprising:
   (a) adding to the sample an agent which releases adenylate nucleotides from the interior of the cells to be assayed into the medium containing the cells;
   (b) simultaneously or subsequently adding to the sample a bioluminescent reagent comprising luciferin or a derivative thereof and a luciferase, said luciferin or derivative thereof emitting light in a bioluminescent reaction with the luciferase in the presence of ATP;
   (c) after said addition, measuring the intensity of the emitted light so as to determine an ATP concentration, said measurement being designated A;
   (d) after the initial light intensity has reached a substantially constant level, adding a reagent which converts ADP to ATP;
      (i) at that time or immediately before or immediately thereafter, measuring the intensity of the emitted light; said measurement being designated B;
      (ii) subsequently, when the cellular ADP has been converted to ATP, measuring the intensity of emitted light at a level C; and
      (iii) from the difference C–B determining an ADP concentration; and
   (f) using information from the ADP concentration as represented by measurement C–B and the ATP concentration as represented by measurement A to determine the condition of the cells.

7. The method according to claim 6, wherein in step (f) the information is used to determine the condition of the cells as:
   (1) proliferating or having a substantially constant number of viable cells in a state of arrested growth;
   (2) undergoing apoptosis or secondary necrosis; or
   (3) undergoing primary necrosis.

8. The method according to claim 7, wherein the cell condition is determined as follows:

| (C – B): A | Corresponding condition of cells |
|---|---|
| negative or substantially zero = | (1) |
| above substantially zero, up to 2 = | (2) |
| above 2 = | (3) | and "substantially zero" means the same as corresponding normal control cells or within 10% thereof.

9. The method according to claim 8, which further comprises distinguishing growth-arrested cells in G2/M phase of the cell cycle from proliferating or control cells by the higher ATP concentration represented by A in the growth-arrested cells, and by a lower ADP:ATP ratio, represented by (C–B):A in the growth-arrested cells.

10. The method according to claim 7, which further comprises carrying out a second assay as defined in claim 7, but without nucleotide-reducing step (a) and distinguishing secondary necrosis from apoptosis by the higher ADP concentration represented by light intensity measurement difference C–B in the necrotic cells in the second assay when the nucleotide-releasing step is omitted, compared with the first assay when the nucleotide-releasing step is carried out.

11. The method according to claim 1, carried out on a sample of volume 240 microliters or less.

12. The method according to claim 1, wherein the molar concentration of ATP in the sample is $10^{-6}$ or higher.

13. A kit for carrying out an assay of the physical condition of a sample of biological cells in vitro, in a medium for maintaining the cells, comprising:
   (1) a bioluminescent reagent comprising luciferin or a derivative thereof and a luciferase, said luciferin or derivative thereof emitting light in a bioluminescent reaction with the luciferase in the presence of ATP;

(2) a reagent or reagents which converts cellular ADP to ATP and is effective to enable the concentration of ADP to be determined by measurement of the light emitted by ATP in said bioluminescent reaction; and (3) buffer for reconstituting, diluting or dissolving the bioluminescent and ADP-converting reagents, said components (1), (2) and (3) being present in proportions not exceeding those required to carry out a predetermined number of assays in an assay volume not exceeding 240 μl, provided that the buffer may be present in the kit in an excess of up to 80% by volume of its required proportion.

14. The kit according to claim 13, wherein the excess of buffer does not exceed 50% by volume of its required proportion.

15. The kit according to claim 13, wherein the bioluminescent and ADP-converting reagents are provided in the form of a number of separate measured doses, each dose being the amount required for one assay.

16. The kit according to claim 13, wherein the ADP-converting reagent comprises a partial inhibitor of the luminescent reaction.

17. The kit according to claim 13, wherein the ADP-converting reagent comprises phosphoenol pyruvate and pyruvate kinase in amounts which provide concentrations thereof immediately before addition to the assay of 1.7 to 50 mM phosphoenol pyruvate and 8.3 to 250 U/ml of pyruvate kinase.

18. The kit according to claim 13, wherein the ratio of Units of pyruvate kinase to micromoles of phosphoenol pyruvate is from 2:1 to 8:1.

19. The kit according to claim 13, which further comprises a reagent for releasing adenylate nucleotides from the interior of the cells.

20. A reagent for converting ADP to ATP which comprises phosphoenol pyruvate and pyruvate kinase in a ratio of from 2:1 to 8:1 Units PK: 1 micromole PEP.

* * * * *

UNITED STATES PATENT AND TRADEMARK OFFICE
CERTIFICATE OF CORRECTION

PATENT NO. : 6,004,767
DATED : December 21, 1999
INVENTOR(S) : CROUCH et al

It is certified that error appears in the above-indentified patent and that said Letters Patent is hereby corrected as shown below:

Column 20, line 16, delete "Claim 20".

Signed and Sealed this

Eighth Day of May, 2001

Attest:

NICHOLAS P. GODICI

Attesting Officer    Acting Director of the United States Patent and Trademark Office